United States Patent [19]

Fleckenstein et al.

[11] Patent Number: 4,902,290

[45] Date of Patent: Feb. 20, 1990

[54] PROCESS FOR THE PREPARATION OF A VESSEL PROSTHESIS IMPREGNATED WITH CROSSLINKED GELATIN

[75] Inventors: Peter Fleckenstein, Fuldabrück; Heinz-Helmut Werner, Melsungen, both of Fed. Rep. of Germany

[73] Assignee: B. Braun-SSC AG, Emmenbrucke, Switzerland

[21] Appl. No.: 226,434

[22] Filed: Jul. 29, 1988

Related U.S. Application Data

[62] Division of Ser. No. 21,129, Mar. 3, 1987, Pat. No. 4,784,659.

[30] Foreign Application Priority Data

Mar. 12, 1986 [DE] Fed. Rep. of Germany ....... 3608158

[51] Int. Cl.[4] .................................... A61F 2/06

[52] U.S. Cl. .................................... 623/1; 623/901; 128/DIG. 8; 427/2

[58] Field of Search .................... 623/1, 11, 12, 901; 427/2, 423, 426; 128/DIG. 8

[56] References Cited

U.S. PATENT DOCUMENTS

| | | | |
|---|---|---|---|
| 3,106,483 | 10/1963 | Kline et al. | 424/423 |
| 4,060,081 | 11/1977 | Yannas et al. | 623/1 |
| 4,167,045 | 9/1979 | Sawyer | 623/2 |
| 4,747,848 | 5/1988 | Maini | 623/1 |
| 4,749,689 | 6/1988 | Miyata et al. | 128/DIG. 8 |

FOREIGN PATENT DOCUMENTS

| | | |
|---|---|---|
| 3020611 | 1/1983 | Fed. Rep. of Germany . |
| 2153235 | 8/1985 | United Kingdom . |

OTHER PUBLICATIONS

Abstract of Pat. No. DT-1494939 to Buddecke published Mar. 3, 1972.

*Primary Examiner*—V. Millia
*Assistant Examiner*—Paul Prebilie
*Attorney, Agent, or Firm*—Herbert Dubno

[57] ABSTRACT

The invention relates to a process to prepare vessel prostheses formed from a porous basic body and an impregnating coating of crosslinked gelatin for sealing the pores.

Crosslinking takes place accompanied by the use of a diisocyanate. The impregnating coating has good mechanical and physiological properties.

10 Claims, No Drawings

PROCESS FOR THE PREPARATION OF A VESSEL PROSTHESIS IMPREGNATED WITH CROSSLINKED GELATIN

This is a divisional of application Ser. No. 021,129 filed on 3 March 1987 now U.S. Pat. No. 4,784,659.

FIELD OF THE INVENTION

The present invention relates to a vessel prosthesis which is in itself porous, but is sealed by impregnating with crosslinked gelatin and to a process for the production thereof.

BACKGROUND OF THE INVENTION

Vessel prosthesis for replacing hollow organs in humans and animals and in particular blood vessels have long been known. They are generally made from textile material and in particular a knitted fabric (DE-A2-26 13 575 corresponding to U.S. Pat. No. 4,047,252, DE-A2-20 09 349 corresponding to U.S. Pat. No. 3,945,052 and DE-A1-24 61 370 corresponding to U.S. Pat. No. 3,878,565). However they can also be made from non-textile materials (EP-A1-0 106 496 and BG-A1-15 06 432). In general, the vessel prosthesis are porous, so as to permit a growing in of the tissue for obtaining conditions which are as natural as possible. However, since after the implantation of the prosthesis, these pores frequently lead to undesirably high body fluid loseses, it is desirable to seal said pores with a material resorbable by the body and which is successively replaced by the growing in tissue.

It is known from DE-A2-14 94 939 to use procollagen as the impregnating agent, which is applied to the porous prosthesis in acid solution and then rendered insoluble by increasing the pH-value.

The use of collagen for sealing is known from DE-A2-14 91 218, U.S. Pat. No. 4,167,,045, DE-A1-34 03 127 and De-A1-35 03 126. The crosslinking of collagen normally takes place with aldehydes, particularly formaldehyde.

It is also known to impregnate porous vessel prostheses with soluble gelatin and to crosslink the same (DE-A2-14 94 939), crosslinking taking place with the aid of thiol group-containing compounds with subsequent oxidative crosslinking, accompanied by the formation of disulphide bridges.

High demands are made on the characteristics of the impregnating coating, which must adhere well to the prosthesis body, provide a good sealing thereof, be ealstic and in particular not release any harmful products during resorption. The known impregnated prostheses only partly fulfil these requirements. In addition, they are far from easy to produce, or expensive starting materials are required, which is prejudicial to industrial manufacture.

OBJECT OF THE INVENTION

The object of the present invention is therefore to provide an impregnated vessel prosthesis, which is easier to manufacture, has good mechanical characteristcs and is completely tight, is not harmful for the receiver organism and can be easily handled, particularly during implantation.

DESCRIPTION OF THE INVENTION

This problem is solved by a vessel prosthesis which is porous as such, but is sealed by impregnating it with crosslinked gelatin and wherein the gelatin is crosslinked with a diisocyanate.

Isocyanates react with the reactive nucleophilic groups of gelatin, particularly the amino groups and also the hydroxyl groups, accompanied by the formation of stable bonds and crosslinking products. Crosslinking with diisocyanates is irreversible in contrast to crosslinking with aldehydes, in which there is a state of equilibrium, so that aldehydes re-form and are released again. At the end of the reaction there are no longer any isocyanate residues and they are also not reformed from the crosslinking product. A gelatin crosslinked with diisocyanate forms a tight impregnation with good mechanical characteristics, so that in relation to the porosity of the vessel prosthesis little gelatin and crosslinking agent is required, but nevertheless a complete seal is obtained.

The crosslinking of biological material with diisocyanates is known per se. Thus, DE-A2-27 34 503 describes a process for producing a collagen sponge, in which a paste or slurry of partly decomposed collagen is mixed with diisocyanate, shock-frozen to temperatures of $-10°$ to $-30°$ C., left at temperatures below 0° C., washed, subsequently treated and then dried. This gives a soft, porous foam or sponge. In a process known from DE-A2-30 20 611 Achilles' tendons are macerated and reduced to fibers, after which the fibers are crosslinked using hexamethylene diisocyanate emulsified in an aqueous saline solution and then inter alia knittable yarns are produced from the crosslinked fibers. However, these processes are in no way linked with the problem of the invention.

The vessel prosthesis which is porous as such can have a porosity of approximately 2000 $cm^3/min/cm^2$. As a result of the inventive impregnating coating of gelatin mixed with diisocyanate, it is possible to completely eliminate this porosity. The decomposition of the thus crosslinked gelatin in the body is slowed down to coincide with the rate at which the new tissue grows into the porous body of the vessel prosthesis and ensures natural sealing.

The porous body of the vessel prosthesis can have the conventional structure of a textile vessel prosthesis, e.g. a smooth warp knitted fabric according to German Pat. No. 20 09 349, the structure of a onesided velour prosthesis according to U.S. Pat. No. 38 78 565 or that of a double velour prosthesis according to German Pat. No. 26 13 575. However, the prosthesis can also be a porous, non-textile prosthesis, e.g. of stretched polytetrafluoroethylene, as described in British Pat. No. 15 06 432. The prosthesis structures bounding the pores are coated with a thin crosslinked gelatin film for sealing purposes, the pores being closed by thin gelatin membranes. As a result of the film-like coating of the individual structural elements of the vessel prosthesis and the joining thereof by membranes, a seal is obtained which differs from a coating completely filling or covering the porosity. For example, in the case of textile prostheses, individual fibers or fiber bundles or strands are coated with a film of crosslinked gelatin and through the membranes are interconnected over and beyond the cavities between the fibers or strands and namely in different planes within the vessel prosthesis wall. As a result of this fine structure the vessel prosthesis handling is improved rather than impaired by the impregnation.

The good sealing of the vessel prosthesis when using only a little impregnating material is also made possible in that gelatin is a material present in the form of a homogeneous solution, as opposed to collagen which is a heterogeneous fibrous material and is not therefore completely tight in thin layer form. The weight rati of porous prosthesis body to impregnating coating can be in the range 1:02. to 1:3, particularly approximately 1:1, including the further additives optionally present in the impregnating coating such as plasticizers. Hydrophilic plasticizers, particularly glycerol and other known polyols are used with advantage, to prevent a complete drying out of the impregnating coating and to improve the elasticity thereof. The moisture content of the impregnating coating in the dried state is preferably in the range 15 to 25% by weight, especially 17 to 22% by weight, based on the weight of the crosslinked impregnating coating.

The preferred crosslinking agent is hexamethylene diisocyanate. However, it is also possible to use other diisocyanates, particularly aliphatic diisocyanates with 4 to 12 carbon atoms and preferably 6 to 10 C-atoms. As opposed to formaldehyde, it has been found that a greater chain length crosslinking agent is more favorable for the elasticity of the product due to the so-called spacer function of the bridges between the protein chains.

The impregnating coating of the vessel prosthesis according to the invention can in known manner contain therapeutically active materials or other active substances. In a particularly preferred embodiment, these materials or active substances are not merely mixed into the impregnating coating and are instead bonded or enclosed in the support or carrier, so that they are only released after time delay. To this end, the impregnating coating and in particular the gelatin can contain constituents which absorb or adsorb the active substances and only gradually release the same. Particularly suitable constituents of this type are exchangers, particularly ion exchangers. In a particularly preferred embodiment of the invention at least part of the gelatin comprises succinylated gelatin, which has such properties. As a result of their basic functions aminoglycosides, such as gentamycin, can be well held by such modified gelatins. As modified gelatin gelatinizes or gels less well than normal gelatin, the modified gelatin proportion is normally dependent on the gelability of the mixture and can be in the range 10 to 50% by weight with respect to the total gelatin quantity. Readily gelable gelatins, such as edible gelatin is preferred (Bloom value 110 to 300, preferably 240 to 280). When crosslinking with diisocyanate the modified gelatin having the exchanger functions is also crosslinked in, so that the therapeutically active material or the active substance adheres to the actual gelatin structure.

The inventive process for producing the impregnated vessel prosthesis is characterized in that a porous vessel prosthesis is impregnated with an aqueous gelatin solution, the gelatin is allowed to gel and then carefully dehydrated, particularly dried in air and then the preimpregnate obtained is crosslinked with diisocyanate.

Diisocyanates react not only with gelatin, but also with compounds having other polar groups, such as e.g. with water and alcohols, accompanied by the formation of undesired by-products, such as insoluble urethane and urea derivatives. Although, as a result of its tightness, the impregnating coating does not allow a washing out of any by-products formed in the coating, as is the case with the known porous fibrous products crosslinked with diisocyanate, it has been found that the tendency of diisocyanates, to form by-products does not have a harmful effect.

For impregnating the porous vessel prosthesis with the gelatin solution, the vessel prosthesis is preferably immersed in the solution. As a result of the application of a vacuum, the pores can be completely filled with the gelatin solution. The gelatin concentration in the solution can vary within wide limits and is preferably between 3 and 20, particularly betwen 5 and 15% by weight of the impregnating solution. However, it is important that there is a homogeneous solution. Impregnation takes place at elevated temperature, i.e. over 40° C., in order to bring about gelling by cooling. As in aqueous solution at temperatures over 60° C., gelatin decomposes when left standing for a long time, the temperatures should not be significantly above this. Therefore temperature ranges between 45 and 70° C., especially 55° and 60° C. are preferred. The impregnating solution can also contain the plasticizer in quantities up to 60% by weight, particularly 10 to 40% by weight. The water content is normally 30 to 97% by weight, preferably 50 to 80% by weight. As a function of the gelability of the gelatin or gelatin mixture, the quantity ratios are so matched with one another that the gelatin is dissolved at the impregnating temperature and the impregnating solution is able to flow, but while ensuring that the gelatin gels on cooling to approximately 20° to 30° C. During cooling the prostheses impregnated with the gelatin solution are preferably moved in order to obtain a uniform coating thickness of the gelled gelatin. For this purpose, the prostheses can be rotated about their longitudinal axis or subject to a tumbling movement after removal from the impregnating bath and after briefly being left to drip.

It is important that the dehydration or dewatering of the gelled gelatin coating or the drying thereof is performed in a careful manner, in order to obtain a good uniformly structured impregnating coating. Air drying at 25 to 35, particularly approximately 30° C. is suitable. The relative humidity of the drying air is preferably between 30 and 50%, particularly approximately 405. Particularly if the prosthesis are immersed in the gelatin solution accompanied by the application of a vacuum, a single impregnation or treatment is sufficient for obtaining a complete tightness, accompanied by the advantage of the resulting low material quantity and favorable mechanical characteristics.

Working takes palce with a diisocyanate excess for crosslinking the gelatin, firstly to obtain a complete gelatin crosslinking and to make it insoluble and secondly in view of the expected secondary reactions. Working preferably takes place without influencing the pH-value. The gelatin can be left at a normal pH-value, which is usually approximately 5.5. The crosslinking reaction can be performed in a pH range of 3.5 to 7.5. Acceptable reaction times of approximately 5 to 10 hours are attainable during crosslinking at ambient temperature, without secondary reactions having a disadvantageous effect and without special measures having to be taken.

It is particularly advantageous for performing the crosslinking reaction to use solutions of diisocyanate in polar organic solvents, which readily wet the predried gelatin impregnating coating. Preference is given to solvents which are miscible with water and plasticizer; isopropanol being particularly suitable. Preferably the solvent makes up 30 to 95% by weight of the crosslinking solution. The diisocyanate diffuses from the crosslinking solution into the gelatin coating and reacts, accompanied by crosslinking, with the gelatin. The diffusion of diisocyanate into the gelatin coating preferably takes place both from the outside and from the inside. For this purpose, the prostheses can advantageously be immersed in the crosslinking solution. Although working takes placed with a considerable diisocyanate excess, which is preferably more than 10 times the stoichiometric quantity needed for crosslinking, the diisocyanate concentration in the crosslinking solution is preferably under 3% by weight, in order to suppress secondary reactions to the greatest possible extent, because diisocyanate is also able to react with components of the crosslinking solution. The diisocyanate concentration can be between 0.03 and 3% by weight, preferably between 0.05 and 0.5% by weight, preference being given to roughly 0.1% by weight. The crosslinking solution preferably also contains plasticizers and/or water in order to introduce the plasticizer and water into the gelatin coating or prevent a washing out of water and/or plasticizer from the gelatin coating during the crosslinking reaction. The concentration of plasticizer, particularly glycerol can be 0 to 60% by weight and in particular 10 to 20% by weight. In extreme cases the water content can be up to 70% by weight, but is normally much lower, namely between 3 and 30% by weight and particularly between 5 and 10% by weight. It is important for the preferred embodiment that the water content is so low that the diisocyanate is present in the dissolved state in the crosslinking solution. Through a relative movement between the crosslinking solution and vessel prosthesis it is possible to ensure that the diisocyanate concentration on the prosthesis surface is kept as high as possible. In a preferred embodiment the crosslinking solution is constantly circulated or pumped around and is simultaneously filtered. Insoluble by-products are continuously removed, so that deposits on the vessel prosthesis and therefore contamination are avoided. The low diisocyanate concentration permits a safe handling of the crosslinking solution. The diisocyanate concentration constantly decreases during the crosslinking reaction, so that safe disposal is possible at the end of the reaction. However, process variants are possible in which working takes place with a substantially constatn diisocyanate concentration.

In a particularly preferred embodiment of the invention the moisture content and preferably also the plasticizer content of the dehydrated, still uncrosslinked, but predried gelatin impregnating coating, together with the water content and preferably also the plasticizer content of the crosslinking solution are adjusted in such a way that they are substantially in equilibrium with one another on immersing the predried impregnated vessel prosthesis in the crosslinking solution. This makes it possible to avoid undesired concentration changes, which could e.g. lead to the leaching or swelling of the not yet crosslinked gelatin impregnating coating.

At the end of crosslinking the gelatin impregnating coating is waterproof, so that it can be washed with water, to which optionally a plasticizer is added and then carefully dried. Sterilization takes place preferably by per se known radiation.

SPECIFIC EXAMPLES

Further features and details of the invention can be gathered from the following description of preferred embodiments. The individual features can be realized alone or in the form of combinations.

EXAMPLE 1

Knitted double microvelour vessel prostheses of polyethylene terephthalate fibers provided with a pleat are fixed in a frame and immersed in an aqueous gelatin impregnating solution containing 7.5% by weight of gelatin and 15% by weight of glycerol as the plasticizer in demineralized water and at a temperature of 60° C.

A vacuum is now applied to the gelatin solution to completely remove the air enclosed in the textile prostheses. Following the rising of the air bubbles, the prostheses are left for approximately 15 minutes in the solution under reduced pressure and the latter is then raised to normal pressure again. The prostheses are then removed from the impregnating solution and are briefly allowed to drip. They are then cooled to normal temperature, accompanied by a slight tumbling movement. Following the gelling of the coating material, the coated prostheses are placed in a climatic chamber and dried in air therein having a relative atmospheric humidity of 40% at 30° C. until the residual moisture content in the impregnating solution is approximately 20%.

The predried prostheses are them immersed in a crosslinking solution containing 0.1% by weight of hexamethylene diisocyanate, 15% by weight of glycerol, 8.5% by weight of water and 76.4% by weight of isopropanol. The coated prostheses are left for 8 hours at ambient temperature in this solution, while the latter is simultaneously constantly pumped around and filtered. At the end of crosslinking the prostheses are removed from the crosslinking solution and washed in water with a 15% glycerol solution, followed by careful drying again at 30° C. and 40% relative atmospheric humidity until there is a residual moisture content of 15 to 20%, based on the impregnating coating. The prostheses are then cut to the nominal length, individually packed and sterilized by radiation.

The prostheses impregnated in this way are completely tight. The impregnating coating is located in the textile fibrous structure and can hardly be seen with the naked eye. The prosthesis has a bright white appearance, is flexible and can be compressed and stretched in the axial direction. Following implantation of the prosthesis, the crosslinked coating material is resorbed at the rate of which the natural tissue subsequently grows, without the decomposition products revealing any harmful effects. The impregnating coating is also both immunologically and toxicologically unobjectionable.

EXAMPLE 2

The procedure of example 1 is repeated, but the edible gelatin is replaced by a mixture of 70% by weight of edible gelatin and 30% by weight of succinylated gelatin. The crosslinked impregnating coating obtained in this way contains additional acid radicals making the impregnating coating suitable for storage, e.g. by diffusion and binding of therapeutic acitve substances with basic characteristics. These therapeutic active substances are only very slowly released following the implantation of the prosthesis, so that e.g. infection protection is provided over a long period.

EXAMPLE 3

Knitted vessel prosthesis of the double velour type formed from polyethylene terephthalate fibres and having a pleat, are secured in a frame as in example 1 and then impregnated with gelatin in an immersion process. The aqueous impregnating solution contains 10% by weight of gelatin and 20% by weight of glycerol, whilst having a temperature of 60° C. As ain example 1, the textile prosthese are thoroughly vented under reduced pressure. Following removal, they are briefly allowed to drip and the frame is tumbled slightly during the gelling phase of the impregnating solution. Following the separating of the coating mass, the impregnated prostheses are transferred into a climatic chamber and, as in exmaple 1, subject to careful intermediate drying until the residual moisture content of the impregnating coating is approximatley 25%. The predried prostheses are then introduced in the clamped state into a crosslinking bath containing 0.2% by weight of hexamethylene diisocyanate, 50% by weight of glycerol, 43.3% by weight of isopropanol and 6.5% by weight of water. As in example 1, the coated prostheses are left in the crosslinking solution for 8 hours at ambient temperature. The subsequent rinsing stage takes place in such a way that the clampled prostheses are exposed for approximately 5 minutes to a 30% aqueous glycerol solution at ambient temperature and in the circulating process. After drying the impregnating coating of the thus produced prostheses has a residual moisture content of approximately 22%.

The coated prosthesis according to example 1 contains

| | |
|---|---|
| 9.5% | by weight of water |
| 22% | by weight of glycerol |
| 18% | by weight of crosslinked gelatin |
| i.e. 49.5% | by weight impregnating coating and |
| 50.5% | by weight porous basic body. |

The prosthesis according to example 3 contains

| | |
|---|---|
| 13% | by weight of water |
| 32% | by weight of glycerol |
| 16% | by weight of crosslinked gelatin |
| i.e. 61% | by weight impregnating coating and |
| 39% | by weight knitted porous prosthesis. |

Based on the total weight of the impregnating coating, the latter generally contains 10 to 30% by weight water 10 to 60% by weight plasticizer and 20 to 60% by weight crosslinked gelatin.

We claim:

1. A process for producing impregnated vessel prostheses, wherein a porous vessel prosthesis is impregnated with an aqueous gelatin solution, the gelatin solution is allowed to gel, the gelatin solution is then carefully partially dehydrated and then the impregnating coating obtained is crosslinked with a diisocyanate.

2. A process according to claim 1, wherein the impregnation of porous vessel prosthesis with the gelatin solution takes place by immersion.

3. A process according to claim 1, wherein porous vessel prosthesis is only impregnated once with the gelatin solution.

4. A process according to claim 1, wherein for crosslinking the gelatin impregnating coating use is made of a solution of diisocyanate in an organic solvent.

5. A process according to claim 1, wherein the gelatin-impregnated vessel prosthesis is immersed in the cross-linking solution and moved relative thereto.

6. A process according to claim 1, wherein the moisture content and also the plasticizer content of the partly dehydrated, not yet crosslinked gelatin impregnating coating is adjusted in such a way so as to be substantially in equilibrium with the moisture content and the plasticizer content of the crosslinking solution.

7. A process according to claim 2, wherein the impregnation takes place by immersion under a vacuum.

8. A process according to claim 1 wherein the moisture content of the partially dehydrated, not yet crosslinked gelatin impregnating coating is adjusted in such a way so as to be substantially in equilibrium with the moisture content of the cross linking solution.

9. A process for producing an impregnated vessel prosthesis, which comprises the steps of:

(a) impregnating a porous vessel prosthesis with an aqueous gelatin solution;

(b) allowing the gelatin solution to gel;

(c) partially dehydrating the gelatin solution to obtain an impregnating coating; and (d) crosslinking the impregnating coating by applying thereto a solution of 0.03 to 3% by weight of diisocyanate, 0 to 60% by weight of plasticizer, 30 to 95% by weight of solvent, and 5 to 70% by weight of water, the quantity ratios being matched to one another so that the diisocyanate is present in the dissolved state.

10. A process for producing an impregnated vessel prosthesis, which comprises the steps of:

(a) impregnating a porous vessel prosthesis with an aqueous gelatin solution;

(b) allowing the gelatin solution to gel;

(c) partially dehydrating the gelatin solution to obtain an impregnating coating; and (d) crosslinking the impregnating coating by applying thereto a solution containing a diisocyanate wherein the crosslinking solution is constantly circulated during the crosslinking reaction and insoluble by-products are removed by filtration.

* * * * *